United States Patent [19]

Ziofsky et al.

[11] 4,047,303
[45] Sept. 13, 1977

[54] GUIDE FOR SETTING UP ARTIFICIAL TEETH

[76] Inventors: Henry Ziofsky, Rte. 55, Eldred, N.Y. 12732; Brett Jason Sinclair, 150-11 72nd Road, Flushing, N.Y. 11367

[21] Appl. No.: 690,146
[22] Filed: May 26, 1976
[51] Int. Cl.² .............................................. A61C 3/00
[52] U.S. Cl. ...................................... 32/40 R; 32/71
[58] Field of Search ........................ 32/40 R, 71, 14 B

[56] References Cited

U.S. PATENT DOCUMENTS

| 1,654,387 | 12/1927 | Stenz | 32/71 |
| 2,169,719 | 8/1939 | Bush | 32/71 |
| 3,878,611 | 4/1975 | Seaman | 32/71 |

*Primary Examiner*—Robert Peshock
*Attorney, Agent, or Firm*—Peter L. Tailer

[57] ABSTRACT

A set of guides are provided for setting up upper and lower artificial teeth on models. Each guide is a strip of flexible, non-elastic material. A center line is formed on each guide with a millimeter scale extending laterally therefrom on each side. The range or average width of the first anterior tooth is marked on each side of the center line, the range of the widths of the three anterior teeth on each side is marked on the guide, and the range of the widths of the four posterior teeth on each side is marked on the guide. An additional thickness is preferably formed at the top center of each strip, the additional thickness having two integral lobes intersecting at a downward facing angle at the center line to rest on the phrenum of a model. Generally longitudinal height lines parallel to each other are inscribed along the upper edge of each strip, and each guide strip has means provided to have it circle a model.

7 Claims, 5 Drawing Figures

GUIDE FOR SETTING UP ARTIFICIAL TEETH

BACKGROUND OF THE INVENTION

1. Field of the Invention

This invention relates to guides and, more particularly, to dental guides for setting up artificial teeth.

2. Description of the Prior Art

Dentists or dental technicians, after impressions are taken, choose artificial teeth to set up in soft wax or the like on a model. At this stage it is very time consuming to get the proper size, aesthetics, centering, arch form, and vertical and horizontal positioning of the artificial teeth.

SUMMARY OF THE INVENTION

This invention provides a set of guides that save a great deal of time for dentists or dental technicians in setting up artificial teeth on a model. The use of the appropriate guide saves considerable trial and error and can cut average set up time from up to forty five minutes to a very few minutes, often less than five minutes. Each guide is of a flexible, non-elastic transparent material with a center line, laterally extending millimeter scales on each guide, and markings indicating the ranges of the widths of given numbers of teeth. Each guide also has means behind which the phrenum of the model should be placed, parallel height lines, and means to fasten the guide about a model.

DESCRIPTION OF THE PREFERRED EMBODIMENTS

Figure 3:
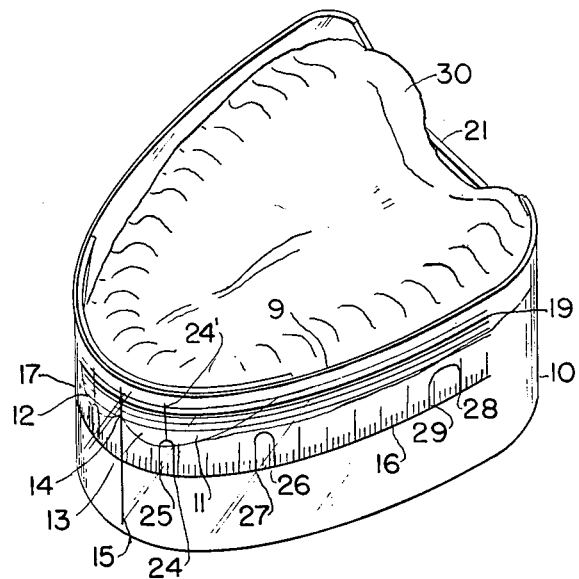
FIG. 3 is a perspective view of the guide of FIG. 1 in place about a model.
Figures 1, 2:
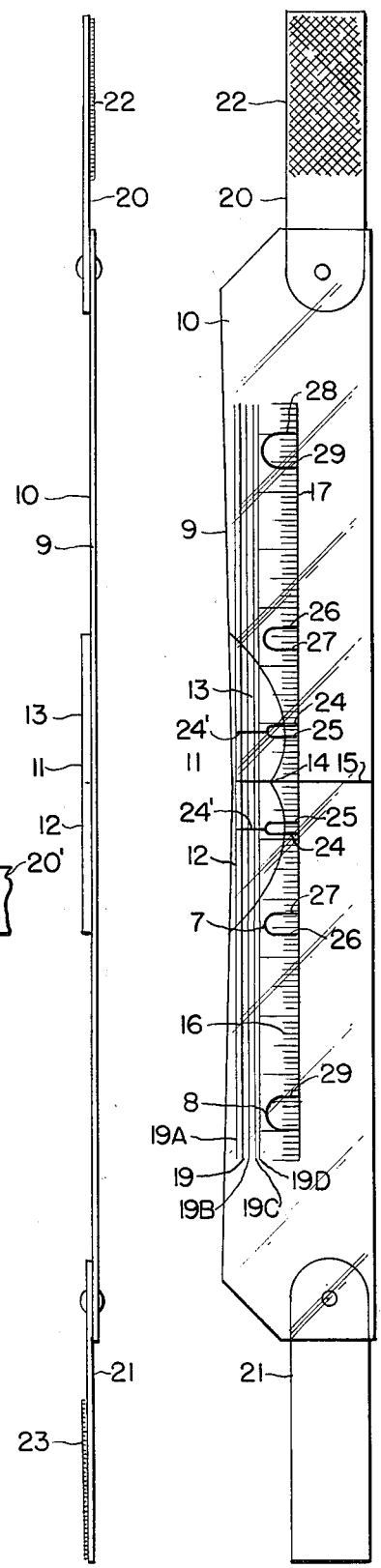
FIG. 1 is a plan view of a dental guide for setting upper teeth according to our invention.
FIG. 2 is an upper edge view of the guide of FIG. 1.

As shown in FIGS. 1, 2, and 3, the guide of this invention for upper teeth is a strip 10 of vinyl about one millimeter thick and it is preferrably transparent. Other suitable material may be used. The upper edge 9 of strip 10 can be slightly concave and its inner surface has an additional thickness 11 of two integral lobes 12 and 13 intersecting to form a downward facing angle 14 at a center line 15. The additional thickness 11 may be another layer of vinyl glued or welded to strip 10. A millimeter scale 16 extends laterally from one side of center line 15 and another scale 17 extends from the other side. Height lines 19, 19A, 19B, 19C, and 19D are parallel to each other and extend along upper edge 9.

The span of the range of the widths of the two first anterior teeth is indicated by the markings 24 and 25 with a line 24' indicating the average width. For a small size scale, only a line 24' indicating the average width would be provided. The span of the range of the three anterior teeth on each side is indicated by the markings 26 and 27. The range of the span or width of the four posterior teeth on each side is indicated by the markings 28 and 29. The upper ends of the markings 26 and 27 may be joined by the curves 7 and the upper ends of the markings 28 and 29 may be joined by the curves 8.

Tabs 20 and 21 are riveted or otherwise fixed to the ends of strip 10 and have Velcro surfaces 22 and 23 formed on or fixed to them. Other fastening means may be used.

This invention is used in the following manner. As shown in FIG. 3, the guide 10 is fixed about a model 30 by means of the fastening means 22 and 23. The downward facing angle 14 centers the guide strip 10 at once as it rests over the phrenum of the model. By visually observing the guide, the technician or dentist can at once select and place the two anterior teeth of the proper width at each side of the center line 15 by using the markings 24 and 25. With great ease and almost no trial and error, the balance of the anterior teeth can be set using the range markings 26 and 27. The set teeth can be tried in a patient's mouth for cosmetic effect if the teeth are being set by a dentist. The posterior teeth can then be set using the markings 28 and 29. In a laboratory, the use of the guide of this invention saves a great deal of time. Further use of this guide and its many advantages will be apparent to one skilled in this art. The guide is preferrably transparent so that the model and set teeth may be seen through it. Although the additional thickness 11 is preferred as it physically engages the phrenum of the model, the lobes 12 and 13 and the angle 14 may be lines inscribed on the guide strip 10 to be lined up with the phrenum of the model.

Figure 4:
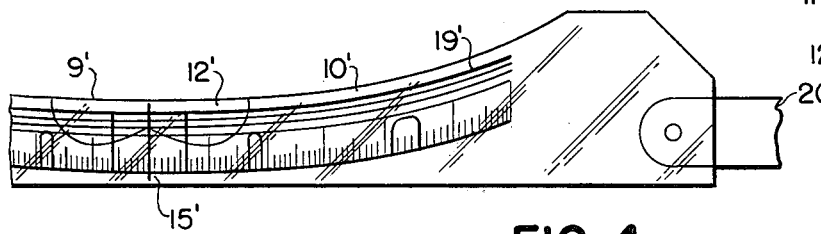
FIG. 4 is a plan view of a fragment of a guide for setting lower teeth.

FIG. 4 shows a guide strip 10' for lower teeth. Strip 10' has a more concave upper edge 9' but is otherwise substantially identical to the guides for upper teeth.

Figure 5:
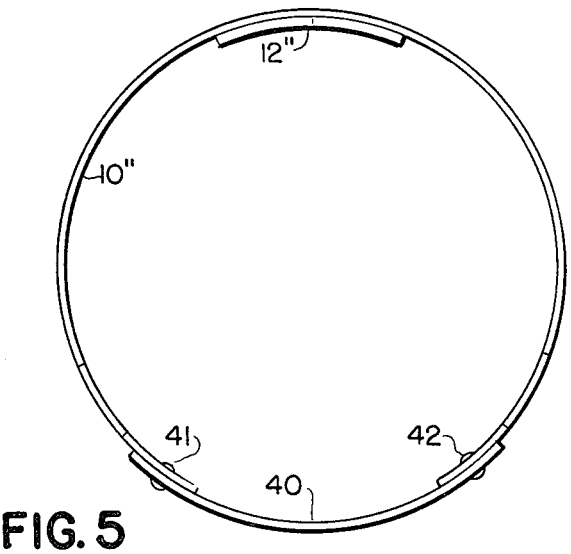
FIG. 5 is a top view of a modified guide.

FIG. 5 shows a guide strip 10" with its ends joined by an elastic 40 fixed by rivets 41 and 42 to allow the guide to be placed about a model.

For all practical purposes, the guides 10 and 10' should each be made in three sizes, small, medium, and large, to accommodate substantially all jaw sizes. When setting up artificial teeth on a model, it is easy to select the appropriate guide from a set.

Suitable markings on sizes of guides are as follows: upper teeth guides, small, medium, and large, respectively, first anterior teeth, average millimeters from the centerline 7, range 7.5–8.5, range 8.5–9.75; three anterior teeth each side range 20.5–23, range 23–26, range 26–30; four posterior teeth each side range 48.5–52, range 54–60, range 61–67; height lines 7–10, 9–11, 10–12; lower teeth guides, small medium, and large, respectively, first anterior teeth, average millimeters from the centerline 4, range 4–5, range 5–6; three anterior teeth each side range 15.5–16.5; range 16.5–18.5; range 18.5–23; four posterior teeth each side range 45.5–48.5, range 49.5–54.5, range 55.5–62; height lines 7–9, 7–10, 8–11.

While this invention has been shown and described in the best form known, it will nevertheless be understood that this is purely exemplary and that modifications may be made without departing from the spirit of the invention.

We Claim:

1. A dental guide for setting up teeth on a model, said guide comprising, in combination, a guide strip of transparent material having an upper edge, a lower edge, and being of flexible, non-elastic material, a vertical center line on said strip, parallel height lines along the upper edge of said strip, first markings on said strip on each side of said center line indicating at least the average width of first anterior teeth, second markings on said strip on each side of said center line indicating the range of the width of the three anterior teeth on each side, measuring scales on said strip extending from said center line toward each end of said guide strip along the lower edge of said strip, indicating means on said strip having a downward facing angle to be placed adjacent to the phrenum of a model, and means joining the ends of said guide strip to fix said guide strip about a model.

2. The combination according to claim 1 with the addition of indicating means to be placed adjacent to the phrenum of a model, said indicating means being an additional thickness having two integral lobes, said downward facing angle formed by the intersection of said lobes, said downward facing angle resting on the phrenum of a model.

3. The combination according to claim 2 with the addition of third markings on said strip on each side of said center line indicating the range of the width of the four posterior teeth on each side.

4. The combination according to claim 3 wherein said means joining the ends of said strip is an elastic.

5. The combination according to claim 3 wherein said means joining the ends of said strip are two mutually engaging fastening elements.

6. The combination according to claim 3 wherein said dental guide is for setting upper teeth on a model, said upper edge of said strip being slightly concave, said dental guide being in three sizes, small size, medium size, and large size; said small size having said first markings 7 mm from said center line, said second markings 20.5 and 23 mm from said center line, and said third markings 48.5 and 52 mm from said center line; said medium size having said first markings 7.5 and 8.5 mm from said center line, said second markings 23 and 26 mm from said center line, and said third markings 54 and 60 mm from said center line; and, said large size having said first markings 8.5 and 9.75 mm from said center line, said second markings 26 and 30 mm from said center line, and said third markings 61 and 67 mm from said center line.

7. The combination according to claim 3 wherein said dental guide is for setting lower teeth on a model, said upper edge of said strip being concave, said dental guide being in three sizes, small size, medium size, and large size; said small size having said first markings 4 mm from said center line, said second markings 15.5 and 16.5 mm from said center line, and said third markings 45.5 and 48.5 mm from said center line; said medium size having said first markings 4 and 5 mm from said center line, said second markings 16.5 and 18.5 mm from said center line, and said third markings 49.5 and 54.5 mm from said center line; and, said large size having said first markings 5 and 6 mm from said center line, said second markings 18.5 and 23 mm from said center line, and said third markings 55.5 and 62 mm from said center line.

* * * * *